(12) United States Patent
Chitre et al.

(10) Patent No.: US 6,748,277 B1
(45) Date of Patent: Jun. 8, 2004

(54) MEDICAL CATHETER/LEAD BODY DESIGN AND MEANS OF MANUFACTURE THEREOF

(75) Inventors: Yougandh Chitre, Valencia, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 275 days.

(21) Appl. No.: 09/977,882

(22) Filed: Oct. 11, 2001

(51) Int. Cl.⁷ .................................................. A61N 1/00
(52) U.S. Cl. ..................................................... 607/122
(58) Field of Search ............................... 607/122, 123, 607/115, 116

(56) References Cited

U.S. PATENT DOCUMENTS

| | | | |
|---|---|---|---|
| 4,548,203 A | 10/1985 | Tacker, Jr. et al. | 128/419 D |
| 4,932,407 A | 6/1990 | Williams | 128/419 D |
| 5,111,811 A | 5/1992 | Smits | 128/419 D |
| 5,235,978 A | 8/1993 | Hirschberg et al. | 607/5 |
| 5,314,430 A | 5/1994 | Bardy | 607/5 |
| 5,350,404 A | 9/1994 | Adams et al. | 607/5 |
| 5,366,494 A | 11/1994 | Holleman et al. | 607/119 |
| 5,411,524 A | 5/1995 | Rahul | 607/4 |
| 5,411,529 A | 5/1995 | Hudrlik | 607/5 |
| 5,423,865 A | 6/1995 | Bowald et al. | 607/5 |
| 5,431,683 A | 7/1995 | Bowald et al. | 607/5 |
| 5,466,254 A | 11/1995 | Helland | 607/123 |
| 5,531,764 A | 7/1996 | Adams et al. | 607/5 |
| 5,662,697 A | 9/1997 | Li et al. | 607/122 |
| 5,720,768 A | 2/1998 | Verboven-Nelissen | 607/9 |
| 5,800,465 A | 9/1998 | Thompson et al. | 607/9 |
| 5,814,079 A | 9/1998 | Kieval | 607/4 |
| 5,814,081 A | 9/1998 | Ayers et al. | 607/5 |
| 5,836,975 A | 11/1998 | DeGroot | 607/5 |
| 5,836,976 A | 11/1998 | Min et al. | 607/6 |
| 5,865,838 A | 2/1999 | Obel et al. | 607/5 |
| 5,902,324 A | 5/1999 | Thompson et al. | 607/9 |
| 5,902,329 A | 5/1999 | Hoffmann et al. | 607/121 |
| 5,913,887 A | 6/1999 | Michel | 607/123 |
| 5,935,159 A * | 8/1999 | Cross et al. | 607/116 |
| 5,964,795 A | 10/1999 | McVenes et al. | 607/122 |
| 5,968,079 A | 10/1999 | Warman et al. | 607/5 |
| 5,987,354 A | 11/1999 | Cooper et al. | 607/5 |
| 6,006,131 A | 12/1999 | Cooper et al. | 607/5 |
| 6,041,256 A | 3/2000 | Michel | 607/5 |
| 6,055,457 A | 4/2000 | Bonner | 607/126 |
| 6,070,101 A | 5/2000 | Struble et al. | 607/9 |
| 6,070,104 A | 5/2000 | Hine et al. | 607/123 |
| 6,169,921 B1 | 1/2001 | KenKnight et al. | 607/4 |
| 6,205,357 B1 | 3/2001 | Ideker et al. | 607/14 |
| 6,249,700 B1 | 6/2001 | Alt | 607/4 |

(List continued on next page.)

FOREIGN PATENT DOCUMENTS

| | | | |
|---|---|---|---|
| EP | 0813889 A2 | 12/1997 | A61N/1/368 |
| WO | WO00/33914 | 6/2000 | A61N/1/368 |

*Primary Examiner*—Angela D. Sykes
*Assistant Examiner*—Roderick Bradford

(57) ABSTRACT

An implantable endocardial lead includes a first elongated tubular component of flexible resilient material with a first face and a first longitudinally extending channel forming a partial lumen in the first face, a similar second elongated tubular component with a second face opposite the first face and a second longitudinally extending channel forming a partial lumen in the second face, the first and second tubular components being integrated by contiguously uniting the first and second faces with the first and second partial lumina being in mutually overlying relationship forming a full lumen within the elongated lead body. Elastic or inelastic rings received in longitudinally spaced annular grooves provided in the outer peripheral surface of the elongated lead body bias together the first and second elongated tubular components. An elongated electrical conductor is received in the full lumen and an overlying sheath is in contiguous engagement with the peripheral outer surface.

13 Claims, 4 Drawing Sheets

U.S. PATENT DOCUMENTS

| | | |
|---|---|---|
| 6,249,709 B1 | 6/2001 | Conger et al. .............. 607/122 |
| 6,266,563 B1 | 7/2001 | KenKnight et al. ............ 607/5 |
| 6,339,724 B1 | 1/2002 | Thong ......................... 607/28 |
| 6,434,428 B1 | 8/2002 | Sloman et al. ................ 607/28 |
| 6,434,430 B2 | 8/2002 | Borgersen et al. .......... 607/122 |
| 6,456,881 B1 | 9/2002 | Bornzin et al. ............... 607/27 |
| 6,490,486 B1 | 12/2002 | Bradley ....................... 607/28 |
| 6,490,489 B2 | 12/2002 | Bornzin et al. ............. 607/122 |
| 6,493,583 B1 | 12/2002 | Levine et al. .................. 607/9 |
| 6,587,720 B2 | 7/2003 | Hsu et al. ...................... 607/4 |
| 2002/0103507 A1 | 8/2002 | Helland ......................... 607/5 |
| 2003/0023271 A1 | 1/2003 | Hsu et al. ...................... 607/4 |

\* cited by examiner

MEDICAL CATHETER/LEAD BODY DESIGN AND MEANS OF MANUFACTURE THEREOF

FIELD OF THE INVENTION

The present invention relates generally to medical electrical leads, and, more particularly, to implantable medical leads for connecting a stimulation device such as a pacemaker or defibrillator to a heart.

BACKGROUND OF THE INVENTION

Present day cardiac stimulation leads are required to not only have multiple conductors to serve multiple electrodes but they also need to have various sections be of different stiffness or flexibility. However, current lead bodies employ one extruded tubing with one or more lumen to carry conductors. They do not meet the current requirements for the new types of leads such as combinations of pacing/defibrillation and combination left and right side leads.

Typically, implantable medical leads carry multiple conductors and, as such, have previously either employed lead bodies formed of extruded, multiple lumen tubing or have employed a coaxial structure, in which single lumen tubes are mounted coaxially around one another to define multiple lumens in which conductors may be located.

One instance of a recent improved design of lead body is disclosed in U.S. Pat. No. 5,935,159 to Cross, Jr. et al. In this instance, the lead body is formed of separate parts including an extruded core or strut member which is provided with longitudinally extending grooves in which conductors may be located and an outer tubing member, surrounding the core. The outer tubing and the core together define multiple lumens in which conductors may be located. This construction was said to simplify the manufacture of a lead, as it allows the conductor simply to be laid in the elongated grooves of the core, rather than requiring that they be pushed or pulled along the lengths of preformed lumens. In some embodiments of that earlier invention, the core is provided with a central, reinforcing strand, extending along the length of the lead, providing for structural integrity and high tensile strength. The core may be manufactured as a single extrusion, extending the entire length of the lead, or may take the form of sequentially aligned multiple extrusions of differing materials to provide for differential flexibility along the length of the lead.

It was in light of the foregoing that the present invention was conceived and has now been reduced to practice.

SUMMARY OF THE INVENTION

An implantable endocardial lead includes a first elongated tubular component of flexible resilient material with a first face and a first longitudinally extending channel forming a partial lumen in the first face, a similar second elongated tubular component with a second face opposite the first face and a second longitudinally extending channel forming a partial lumen in the second face, the first and second tubular components being integrated by contiguously uniting the first and second faces with the first and second partial lumina being in mutually overlying relationship forming a full lumen within the elongated lead body. Elastic rings received in longitudinally spaced annular grooves provided in the outer peripheral surface of the elongated lead body bias together the first and second elongated tubular components. An elongated electrical conductor is received in the full lumen and an overlying sheath is in contiguous engagement with the peripheral outer surface.

The invention presented in this disclosure is an improvement over the Cross, Jr. et al. lead design discussed above. The present invention allows two or more extrusions to be fitted together axially, after the conductors are placed in their respective lumina. Properties of stiffness or flexibility along the catheter/lead length can be altered in one of two ways:

1) lengths of such extrusions with different properties, for example shore hardness, can be added together to form an inner construction for a lead; and 2) the distance between the annular grooves can be altered; those regions at which the elastic rings engaged in the annular grooves are placed further apart will have greater flexibility than those regions at which the elastic rings engaged in the annular grooves are placed nearer together.

Subsequently, as above noted, an outer extruded tubing or a sheath can be fitted over the inner body construction to constitute a lead body.

According to the invention, then, assembly of the lead body could entail, but need not necessarily be restricted to the following operation steps:

1. The conductors, that is coated or uncoated cable or coil are placed into the appropriate lumen or lumina of half-tubing, made of a suitable medical grade implantable material, for example silicone, polyurethane, or a suitable combination thereof. The tubing may have a single lumen or a plurality of lumina at given cross-sections along the length of the catheter or lead.

2. The other half of the tubing is placed over the first half while ensuring that the grooves of the two halves of the tubing are aligned. A ring made of a suitable elastic material may be slid over the insulation material and into the grooves. Alternatively, a medical grade adhesive or other suitable bonding agent could be used to bond the two halves of the tubing together.

3. Additionally, an outer sheath, made of a suitable material such as silicone, polyurethane, or a combination thereof may be slid over the lead body sub-assembly to hold all its components in place. Numerous cross sections of a catheter or lead body can employ this method of assembly.

By increasing or decreasing the number of grooves and subsequently the number of rings a lead body can hold, the flexibility for different sections along the length of the catheter or lead body can be altered as desired.

A primary feature, then, of the present invention is the provision of an improved technique for manufacturing medical electrical leads, especially implantable medical leads for connecting a stimulation device such as a pacemaker or defibrillator to a heart.

Another feature of the present invention is the provision of such a technique which facilitates the process of manufacture of an implantable medical catheter or lead.

Yet another feature of the present invention is the provision of such a technique according to which flexibility or stiffness can be desirably varied along the length of a catheter or lead body.

Still a further feature of the present invention is the provision of such a technique according to which an elongated lead body of flexible resilient material includes a first elongated tubular component having a first face and a first longitudinally extending channel forming a partial lumen in the first face, a second elongated tubular component having a second face opposite the first face and a second longitudinally extending channel forming a partial lumen in the second face, the first and second elongated tubular components being integrated by contiguously uniting the first and second faces with the first and second partial lumina being in overlying relationship resulting in a full lumen within the elongated lead body.

Yet a further feature of the present invention is the provision of such a technique according to which the elongated lead body has a peripheral outer surface with a pair of longitudinally spaced annular grooves therein and an elastic ring is received in each of the annular grooves for biasing together the first and second faces of the first and second elongated tubular components.

Still another feature of the present invention is the provision of such a technique according to which an elongated electrical conductor is received in the full lumen.

Yet another feature of the present invention is the provision of such a technique according to which the first and second faces are bonded together by adhesive.

Still a further feature of the present invention is the provision of such a technique according to which the elongated lead body has a peripheral outer surface and includes an overlying sheath in contiguous engagement with the peripheral outer surface.

Yet a further feature of the present invention is the provision of such a technique according to which an elongated lead body of flexible resilient material includes first and second elongated tubular components having mutually opposed faces with at least one of the tubular components having a longitudinally extending lumen, the tubular components being integrated by contiguously uniting the first and second faces.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
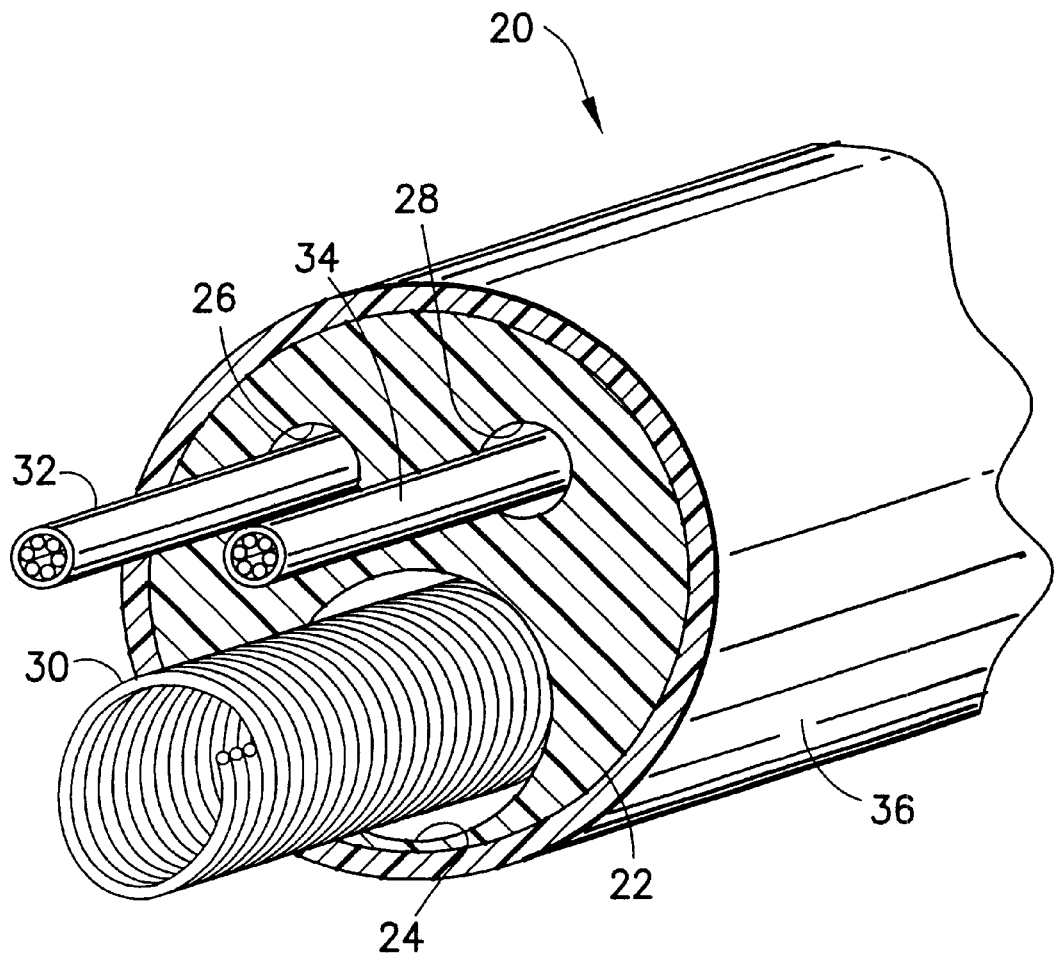
FIG. 1 is a is a perspective view, partially cut away and shown in section, of a known implantable cardiac lead.

Turn now to the drawings and, initially to FIG. 1 which generally illustrates a typical known implantable cardiac lead 20 which includes an insulating lead body 22 with longitudinally extending lumina 24, 26, and 28 generally of circular cross section. The cardiac lead 20 may utilize either a type of silicone rubber or a type of polyurethane as its primary insulation material. A PTFE-coated conductor coil 30 is received in the lumen 24 for connection to a distal electrode (not shown) and redundant ETFE (ethylene-tetrafluoroethylene) coated cable conductors 32, 34 are received in the lumina 26, 28, respectively, for connection to a ring electrode (not shown). Construction of the lead 20 is completed with the application of an outer polyurethane sheath 36 overlying the insulating sheath 22.

It was earlier noted that present day cardiac stimulation leads are required to not only have multiple conductors to serve multiple electrodes but they also need to have various sections be of different stiffness or flexibility. However, current lead bodies employ one extruded tubing with one or more lumen to carry conductors. They do not meet the current requirements for the new types of leads such as combinations of pacing/defibrillation and combination left and right side leads. It is in this context and also in the context of simplifying the construction and fabrication of such leads that the following description is presented.

Further, although the present invention will be described with reference to the embodiments shown in the drawings, it should be understood that the present invention can be embodied in many alternate forms or embodiments. In addition, any suitable size, shape or type of elements or materials could be used.

Figure 2:
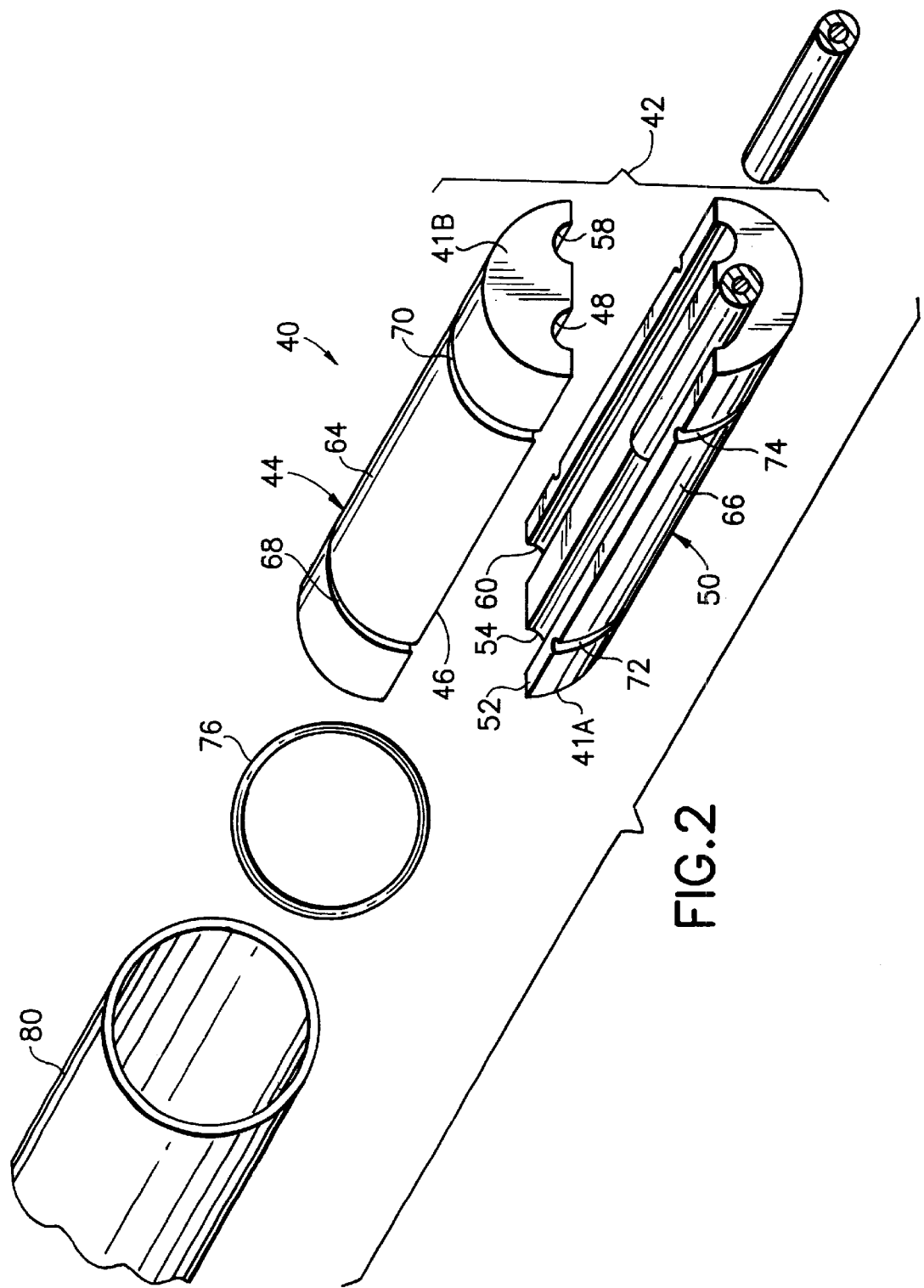
FIG. 2 is an exploded perspective view of an epicardial or endocardial lead embodying the present invention.
Figure 3:
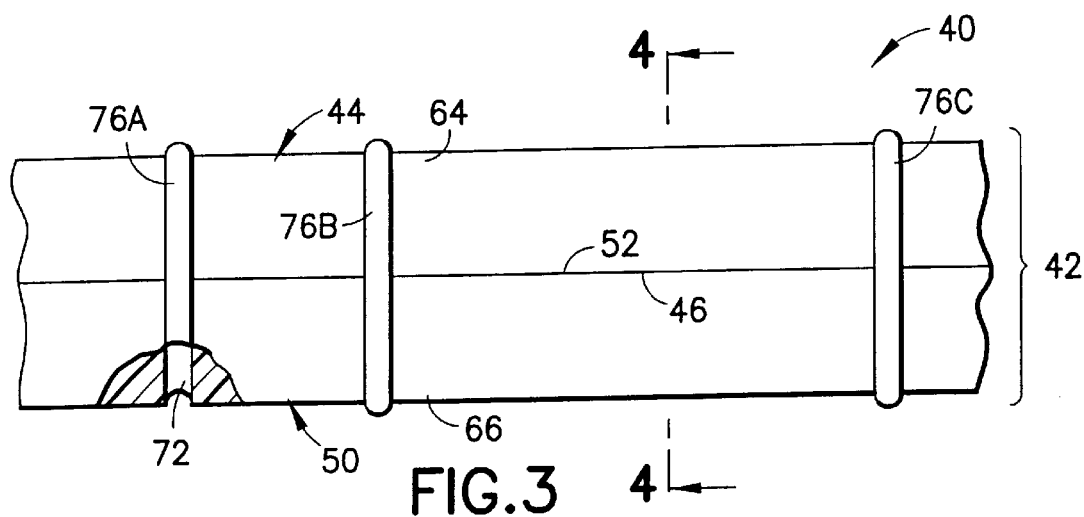
FIG. 3 is a side elevation view of an assembled epicardial or endocardial lead embodying the present invention.
Figure 4:
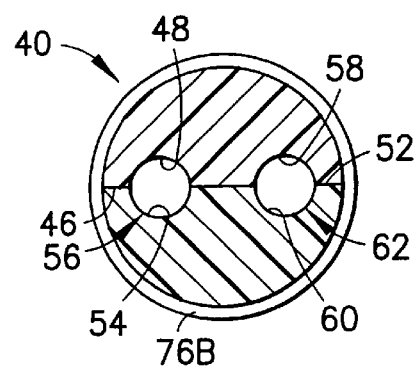
FIG. 4 is a cross-section view taken generally along line 4—4 in FIG. 3.

Turn now initially to FIGS. 2, 3, and 4 which illustrates an implantable epicardial or endocardial lead 40 extending between proximal and distal ends 41a, 41b, respectively, for use with a cardiac stimulation device (not shown) in a customary manner. The lead 40 has an elongated lead body 42 of flexible resilient material such as silicone rubber, polyurethane, or a combination thereof, and includes a first elongated tubular component 44 having a first face 46 and a first longitudinally extending channel 48 forming a partial lumen in the first face. The lead 40 also includes a second elongated tubular component 50 having a second face 52 opposite the first face 46 and a second longitudinally extending channel 54 forming a partial lumen in the second face. The first and second elongated tubular components 44, 50 are subsequently integrated by contiguously uniting the first and second faces 46, 52 with the first and second partial luminae (channels 48, 54) being in mutually overlying relationship resulting in a full lumen 56 (FIG. 4) within the elongated lead body 42. The uniting process may be of any suitable nature and include the use of any suitable materials including adhesive, solvent, and heat fusion.

In actual fact, the lead 40 may have multiple luminae. Viewing FIGS. 2 and 4, for example, the first elongated tubular component may have a third longitudinally extending channel 58 in the first face 46 and the second elongated tubular component 50 may have a fourth longitudinally extending channel 60 in the second face 52. In this instance, when the first and second elongated tubular components 44, 46 are subsequently integrated by contiguously uniting the first and second faces 46, 52, the third and fourth partial luminae (channels 58, 60) are positioned in mutually overlying relationship resulting in a second full lumen 62 (FIG. 4) within the elongated lead body 42. It will be understood that while the lead 40 is illustrated with but two full luminae 56, 62, a lead may actually have many more, depending upon its intended use. In this instance, two luminae are described only for purposes of description.

Continuing with the description of the lead 40, each of the first and second elongated tubular components 44, 50 has an outer peripheral surface 64, 66, respectively. A pair of longitudinally spaced semi-annular grooves 68, 70 are formed in the surface 64 and a similar pair of longitudinally spaced semi-annular grooves 72, 74 are formed in the surface 66. When the first and second elongated tubular components 44, 46 are subsequently integrated as earlier explained, the semi-annular grooves 68, 70 of the first elongated tubular component 44 are axially aligned with the semi-annular grooves 72, 74 of the second elongated tubular component 50. Thereupon, as seen in FIGS. 2, 3, and 4, a ring 76A is received in the mating pair 68, 72 of the semi-annular grooves for biasing together the first and second faces 46, 52 of the tubular components 44, 50. In similar fashion, a second ring 76B is received in the mating pair 70, 74 of the semi-annular grooves for assisting the ring 76A in biasing the tubular components together. The rings 76A and 76B may be elastic or rigid and may be of any suitable material such as PTFE, metal, rigid polymer, or an 0-ring of rubber or polyurethane material.

Figure 5:
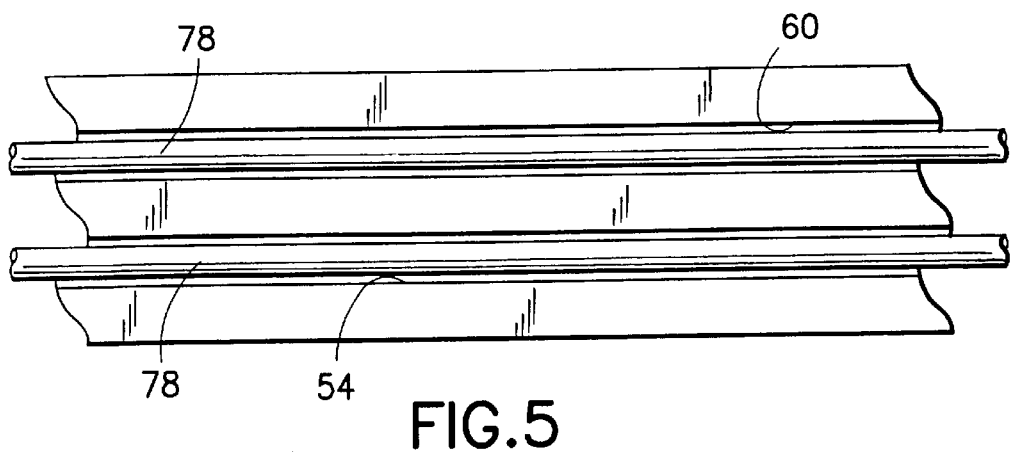
FIG. 5 is a top plan view of the lower elongated tubular component which is illustrated in FIG. 2.

Of course, prior to the uniting process just described, it is necessary to incorporate conductors for transmitting electrical signals from the cardiac stimulation device to body tissue. As seen in FIGS. 2, 4, and 5, a conductor 78 is placed in each of the channels 54, 60 of the second tubular component 50 after which the first tubular component 44 is positioned in overlying relationship with the component 50, then joined together as previously described. For purpose of joinder of the tubular components, it will be understood that the rings 76 need not be used if the uniting process is achieved by the use of materials such as adhesive, solvent, or by the technique of heat fusion.

To complete the construction of the lead 40, it is desirable to apply an overlying sheath 80 (see FIG. 2), typically composed of silicone rubber, polyurethane, or a combination thereof, in contiguous engagement with the outer peripheral surface of the lead body 42 as mutually defined by the surfaces 64, 66.

Another feature of the invention resides in a construction which can be most easily explained with reference to FIG. 3. As seen in FIG. 3, the dimensional spacing between the rings 76A and 76B and their underlying grooves, which can be defined as a first length, is substantially less than the spacing between the rings 76B and 76C and their underlying grooves, which can be defined as a second length. With this construction, it will be appreciated that the flexibility of the lead body is greater along the second length than along the first length. A lead can thereby be designed using this technique to have various flexibilities at various locations along its length. This result can be achieved by using distinct pairs of rings and their underlying grooves or by using a construction as illustrated in FIG. 3 wherein an intermediate ring 76B and its underlying annular groove is common to both the first ring 76A and to the third ring 76C.

Figure 6A:
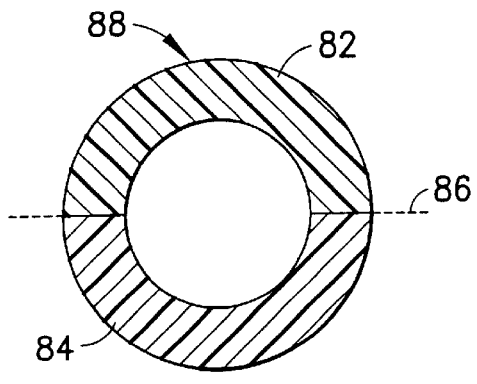
FIGS. 6A, 6B, 6C, 6D, and 6E are detail cross section views illustrating a number of different embodiments of the epicardial or endocardial lead embodying the present invention.
Figure 6B:
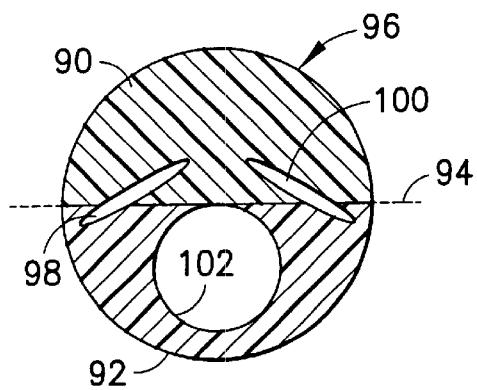
Figure 6C:
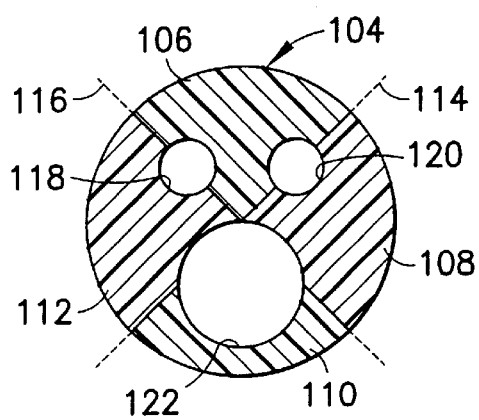
Figure 6D:
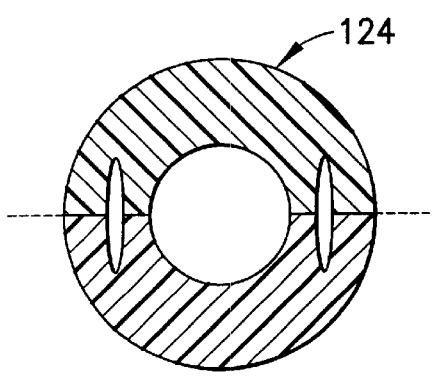
Figure 6E:
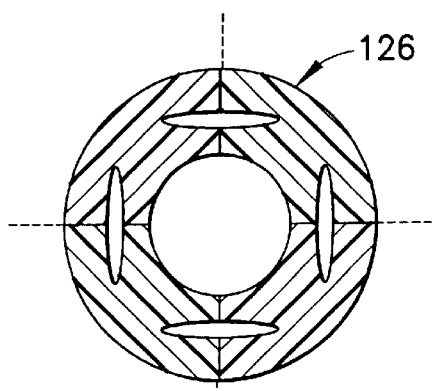

FIGS. 6A, 6B, 6C, 6D and 6E are detail cross section views, each illustrating a different embodiment of an epicardial or endocardial lead embodying the present invention. In FIG. 6A, for example, tubular components 82, 84 are similarly sized and are joined at a plane 86 coincident with a diameter of a cross section of the completed lead 88. In FIG. 6B, tubular components 90, 92 are similarly sized and are joined at a plane 94 coincident with a diameter of a cross section of the completed lead 96. However, in this instance, luminae 98, 100, 102 are of different sizes, shapes and orientations. In FIG. 6C, a completed lead 104 includes four tubular components 106, 108, 110, 112 which are not necessarily similarly sized and are joined at planes 114, 116 not necessarily coincident with diameters of a cross section of the completed lead. Additionally, in this instance, luminae 118, 120, 122 are of different sizes. FIGS. 6D and 6E illustrate leads 124, 126, respectively, of still more designs which would be appropriate for the invention. In a given cross-section of each of the FIGS. 2–6, a portion or whole section of one or more lumens intersects the flat face in one and/or both tubular components. This configuration allows for an elongated electrical conductor to be merely placed or laid in the partial or whole open lumen in the tubular components.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable endocardial lead extending between proximal and distal ends for use with a cardiac stimulation device comprising:
    an elongated lead body of flexible resilient material comprising:
        a first elongated tubular component having a first face and a first longitudinally extending channel forming a partial lumen in the first face;
        a second elongated tubular component having a second face opposite the first face and a second longitudinally extending channel forming a partial lumen in the second face;
        the first and second elongated tubular components being integrated by contiguously uniting the first and second faces to form a planar interface, the first and second partial lumina being in overlying relationship resulting in a full lumen within the elongated lead body;
        wherein the elongated lead body has a peripheral outer surface with a pair of longitudinally spaced annular grooves therein and a second pair of longitudinally spaced annular grooves therein, a first length of the lead body between the first pair of annular grooves being smaller than a second length of the lead body between the second pair of annular grooves; and
        a ring received in each of the annular grooves to bias together the first and second faces of the first and second elongated tubular components;
        wherein the flexibility of the elongated lead body is greater along the second length than along the first length.

2. An implantable endocardial lead as set forth in claim 1:
    wherein the first and second elongated tubular components have a plurality of longitudinally extending channels in the first and second faces, respectively, pairs of the channels in the first and second faces being in overlying relationship such that the elongated lead body has a plurality of full lumina therein.

3. An implantable endocardial lead as set forth in claim 2 comprising an elongated electrical conductor received in each full lumen.

4. An implantable endocardial lead as set forth in claim 1, wherein the ring is elastic.

5. An implantable endocardial lead as set forth in claim 1, wherein the ring is inelastic.

6. An implantable endocardial lead as set forth in claim 1 comprising an elongated electrical conductor received in the full lumen.

7. An implantable endocardial lead as set forth in claim 1, wherein the first and second faces are bonded together by adhesive.

8. An implantable endocardial lead as set forth in claim 1:
wherein the elongated lead body has a peripheral outer surface; and comprising:
an overlying sheath in contiguous engagement with the peripheral outer surface.

9. An implantable endocardial lead as set forth in claim 1, wherein the planar interface radially bisects the united first and second elongated tubular components.

10. An implantable endocardial lead extending between proximal and distal ends for use with a cardiac stimulation device comprising:
an elongated lead body of flexible resilient material comprising:
a first elongated tubular component having a first face and a first longitudinally extending channel forming a partial lumen in the first face;
a second elongated tubular component having a second face opposite the first face and a second longitudinally extending channel forming a partial lumen in the second face;
the first and second elongated tubular components being integrated by contiguously uniting the first and second faces with the first and second partial lumina being in overlying relationship resulting in a full lumen within the elongated lead body;
wherein the elongated lead body has a peripheral outer surface with a first pair of longitudinally spaced annular grooves therein and a second pair of longitudinally spaced annular grooves therein, a first length of the lead body between the first pair of annular grooves being smaller than a second length of the lead body between the second pair of annular grooves; and
further comprising:
an elastic ring received in each of the annular grooves for biasing together the first and second faces of the first and second elongated tubular components;
whereby the flexibility of the elongated lead body is greater along the second length than along the first length.

11. An implantable endocardial lead as set forth in claim 10:
wherein an annular groove is common to both the first pair of longitudinally spaced annular grooves therein and to the second pair of longitudinally spaced annular grooves.

12. An implantable endocardial lead as set forth in claim 10:
wherein an annular groove is common to both the first pair of longitudinally spaced annular grooves therein and to the second pair of longitudinally spaced annular grooves.

13. An implantable endocardial lead extending between proximal and distal ends for use with a cardiac stimulation device comprising:
an elongated lead body of flexible resilient material comprising:
a first elongated tubular component having a first face and a first longitudinally extending channel forming a partial lumen in the first face;
a second elongated tubular component having a second face opposite the first face and a second longitudinally extending channel forming a partial lumen in the second face;
the first and second elongated tubular components being integrated by contiguously uniting the first and second faces with the first and second partial lumina being in overlying relationship resulting in a full lumen within the elongated lead body;
wherein the elongated lead body has a peripheral outer surface with a first pair of longitudinally spaced annular grooves therein and a second pair of longitudinally spaced annular grooves therein, a first length of the lead body between the first pair of annular grooves being smaller than a second length of the lead body between the second pair of annular grooves; and
further comprising:
an inelastic ring received in each of the annular grooves for biasing together the first and second faces of the first and second elongated tubular components;
wherein the flexibility of the elongated lead body is greater along the second length than along the first length.

* * * * *